US00PP25563P3

(12) United States Plant Patent
Ellis

(10) Patent No.: US PP25,563 P3
(45) Date of Patent: May 19, 2015

(54) PECAN TREE NAMED 'ELLIS'

(50) Latin Name: *Carya illinoinensis*
Varietal Denomination: Pecan ELLIS

(76) Inventor: Marvin Elliott Ellis, Vienna, GA (US)

( * ) Notice: Subject to any disclaimer, the term of this patent is extended or adjusted under 35 U.S.C. 154(b) by 0 days.

(21) Appl. No.: 13/374,112

(22) Filed: Dec. 13, 2011

(65) Prior Publication Data

US 2013/0152235 P1 Jun. 13, 2013

(51) Int. Cl.
*A01H 5/08* (2006.01)

(52) U.S. Cl.
CPC ..... *A01H 5/0825* (2013.01)
USPC ..... Plt./153

(58) Field of Classification Search
USPC ..... Plt./153
See application file for complete search history.

*Primary Examiner* — Susan McCormick Ewoldt

(57) ABSTRACT

A new and distinct cultivar of pecan tree, *Carya illinoinensis,* which is characterized by consistent production, high percentage kernel, large nut size, and scab fungus resistance.

5 Drawing Sheets

Botanical classification: *Carya illinoinensis.*
Varietal denomination: Pecan 'ELLIS'.

FIELD OF THE INVENTION

Disclosed herein is a new and distinct variety of pecan tree.

BACKGROUND OF THE INVENTION

The present invention relates to a new and distinct cultivar of the nut-bearing tree *Carya illinoinensis,* known as common pecan and hereafter referred to by the varietal denomination 'ELLIS'. It can be used in gardens or for commercial production of pecan nuts.

The tree was discovered by the inventor in a barnyard near the city of Vienna, Dooly County, Ga. He noted the consistent production, high nut quality, and resistance to scab disease and other pests.

Graft wood of the original 'ELLIS' tree has been propagated by the inventor onto approximately 1200 trees of 'Elliott' rootstock in test orchards in Dooly County, Ga. All horticultural traits observed including leaf shape, color, and morphology, bud form, bark color and texture observed are identical to the parent 'ELLIS' tree, as is normal and expected when pecan trees are propagated by grafting.

Parentage of the tree is unknown. The parent 'ELLIS' tree grew as a seedling from a nut in the yard in which it was discovered. The parent tree was destroyed by a lightning strike in 2005.

SUMMARY OF THE INVENTION

Plants of the cultivar 'ELLIS' have not been observed under all possible environmental conditions. The phenotype may vary somewhat with variations in environment such as light intensity, temperature and cultural conditions, without any variance in genotype.

The following characteristics have been consistently observed and, to the best knowledge of the inventor, their combination form unique characteristics of 'ELLIS' as a new and distinct cultivar:

Harvest date is not exceptionally early but is well within the range of the desired pecan harvest for the early gift pack market. In 2011, shuck split began around October 5 and 50% shuck split occurred on October 12. Nuts were harvested on October 24. This places 'ELLIS' in the same harvest window with such cultivars as 'Desirable' (not patented), 'Elliot' (not patented), and 'Oconee' (not patented), but before that of 'Sumner' (not patented). With marginal care (2 sprays) in 2011, a year of low scab incidence, a one-pound sample of nuts of 'ELLIS' from 15 yr old grafted trees had 47.5 nuts per pound and 59.3% kernel. The sample was collected and graded by Dr. Lenny Wells, University of Georgia Horticulturist. Productivity appears good and comparable to 'Cape Fear' (not patented) based on observations of the cultivars under similar growing conditions at the orchard where 'ELLIS' was evaluated.

Bark is scaly.

Resistance to scab is very good.

Asexual reproduction by the inventor using traditional grafting techniques have shown that the unique characteristics of this new pecan are stable and reproduced true-to-type in successive generations.

BRIEF DESCRIPTION OF PHOTOGRAPHS

Figure 1:
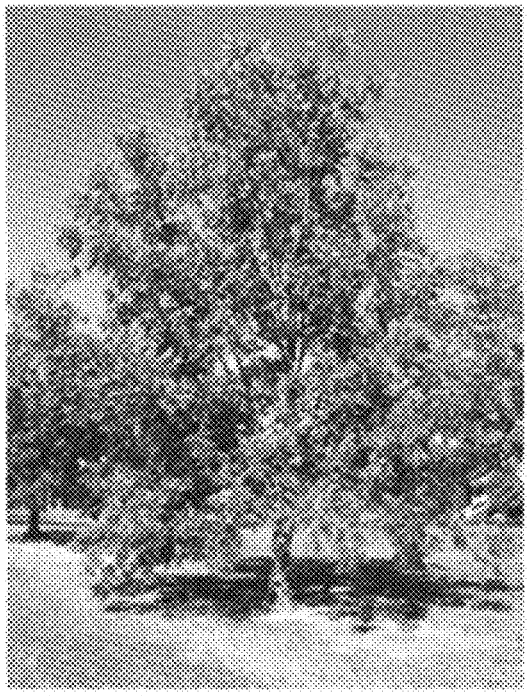

FIG. 1. 'ELLIS' pecan tree, photographed Oct. 16, 2011.

Figure 2:
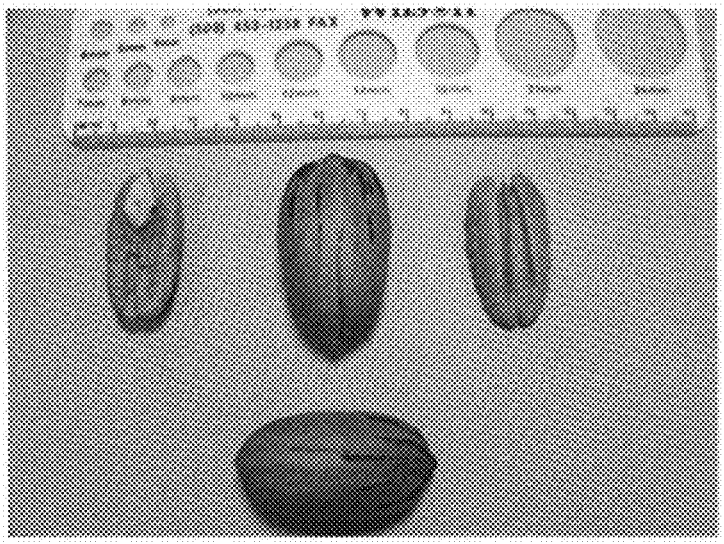

FIG. 2. Kernels (left and right) and inshell nuts (center) of 'ELLIS' pecan. Photographed in 2011.

Figure 3:
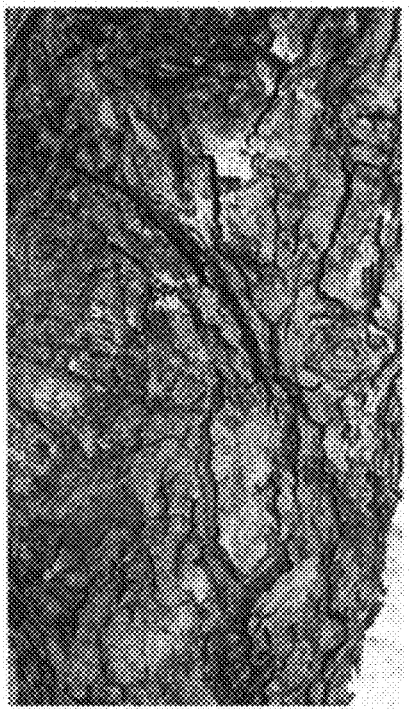

FIG. 3. Bark and trunk of 'ELLIS' pecan tree.

Figure 4:
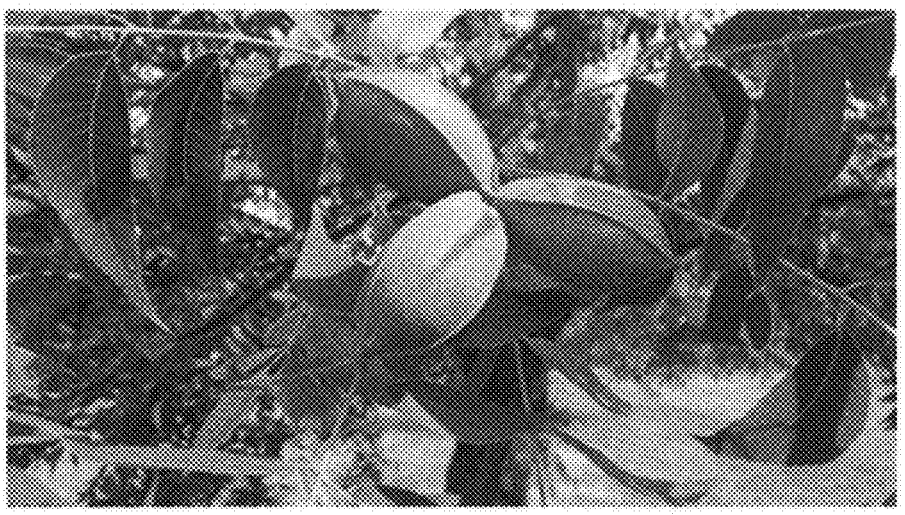

FIG. 4. 'ELLIS' pecan fruit on tree. Note lack of pecan scab incidence on unsprayed tree/Photographed Aug. 19, 2011.

Figure 5:
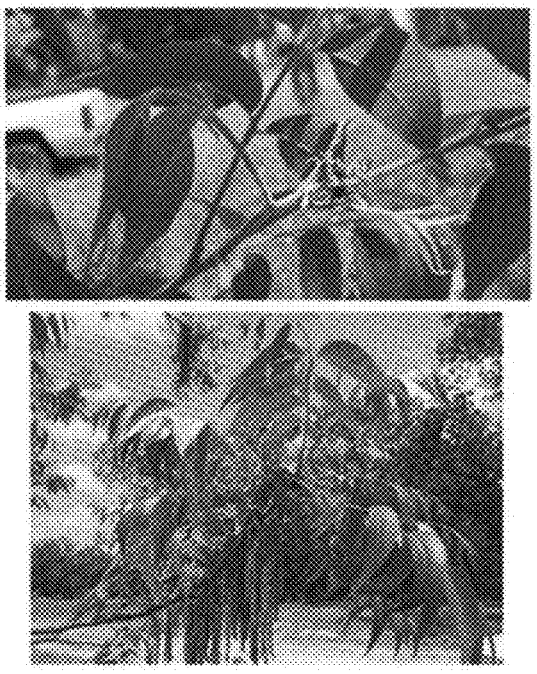

FIG. 5. Cluster of female flowers (top) of 'ELLIS' pecan, and catkins bearing male flowers (bottom). Photographed Apr. 22, 2011 (catkins) and Apr. 29, 2011 (female flowers).

BOTANICAL DESCRIPTION OF THE PLANT

Unless stated otherwise, the botanical description of 'ELLIS' is measured data in April, August, and October 2011 on grafted trees 15 years after grafting onto 'Elliot' rootstock. Average height of trees was 9.1 meters. Canopy spread was 7.9 meters. Trees are pruned as needed to maintain growth as a single central leader tree. Trunk diamater was 71.12 cm. Observational data was in 2010-2011. The trees were grown in Dooly County, Ga. (USDA Zone 7b) under commercial production, except spraying was minimal. The range of day-time growing temperatures was 65-100 degrees F. The range of night-time growing temperature was 50-75 degrees F. Cold hardiness, drought, and heat tolerance appear to be similar to other cultivars such as 'Cape Fear' (not patented) and 'Sumner' (not patented).

The plant is upright in growth habit, similar to 'Pawnee' (not patented), with a modified central leader tree form.

Lenticels are present on bark of twigs. Lenticels are irregular oval-shaped, 1-2 mm in length, and are gray in color. Lenticels are not observable on large branches and on trunk, which is covered with bark.

The stems are green in the tender stage, then brown in the woody stage.

The peduncle is 26.89 mm in length and 3.12 mm in diameter, oval, green in tender stage and greenish-tan in mature stage.

The mature leaf is odd pinnate compound with pinnate leaf venation, deciduous, with dark green shade on upper surface, and light green on lower surface. Leaf vein color is light green. The average length of a mature compound leaf is 31.5 cm., while the average width of a mature compound leaf is 18.7 cm. The average length of an individual leaflet is 10.3 cm., and the average width is 2.8 cm. The leaflet apex is acuminate and narrow. The leaflet base is oblique. The leaflet margin is serrate and the shape is elliptic and falcate, with absent lobes. The leaf arrangement on a stem is alternate, with leaflet venation pinnate. The average number of leaflets on a leaf is 11.

The 'ELLIS' pecan is monoecious, anemophilous and protogynous. Pistillate flowers are borne on a determinate spike, with staminate flowers borne on a determinate pendulous catkin. There are commonly three to six individual pistillate flowers per spike, borne alternately on terminally-positioned spikes. The pistillate flower is symmetrical with no stamens and petals. Pistillate flowers consist of a bilobed stigma on a stigmatic disk surrounded by 3 bracteoles and a bract. The bracteoles and bract are fused at the base to form the involucre or shuck. The pedicels are sessile. The staminate flower or catkin is green with gold pollen. The average length of the catkin is 14.3 cm, average width 0.8 cm. The flower has one pistil, with an oxblood color stigma. The flower has four bracts, which are green, linear lanceolate.

The mature fruit is dehiscent and light green in color. Fruit size, described as size of the mature nut inside the shuck is 5.15 cm in length and 3.19 cm in width. Shuck color is light green. The average weight per nut in 2011, a year of small nut size in Georgia, was 9.7 g. The average nut length was 4.31 cm, while the average width was 2.35 cm. The nut length to width (width midway the length of the nut and across suture) is 2.48 cm. The nut shape is oblong to slightly obovate. The nut base shape is obtuse asymmetric to cuspidate and the nut apex is cuspidate to cuspidate asymmetric. Shuck split was 50% on Oct. 12, 2011. Shells are thin, approximately 0.85 mm. Shell markings are dark, bold and distinct near the tip, but are much less pronounced near the base of the nut.

The following are color descriptions of 'ELLIS,' referencing The Royal Horticultural Society (R.H.S.) Colour Chart (1966).

*Trunk*.—(Mature tree) RHS 198D.
*Winter buds*.—RHS 164B.
*Shoot*.—(Tender stage) RHS 142A.
*Shoot*.—(Woody stage) RHS 196A.
*Lenticels*.—RHS 160D.
*Peduncle*.—(Tender stage) RHS 164C.
*Foliage*.—(Upper surface) RHS 141A.
*Foliage*.—(Lower surface) RHS 144C.
*Catkins*.—RHS 151D.
*Stigma*.—RHS 177A.
*Involucre*.—RHS 150C.
*Shuck*.—RHS 150C.
*Bracts*.—RHS 150C.
*Shell*.—RHS 165B.
*Seed coat*.—RHS 164C.

The invention claimed is:

1. A new and distinct variety of pecan tree named 'ELLIS', substantially as herein described and illustrated.

* * * * *